United States Patent
Manhart

(10) Patent No.: US 11,707,245 B2
(45) Date of Patent: Jul. 25, 2023

(54) QUANTIFICATION OF AN INFLUENCE OF SCATTERED RADIATION IN A TOMOGRAPHIC ANALYSIS

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 330 days.

(21) Appl. No.: 17/076,958

(22) Filed: Oct. 22, 2020

(65) Prior Publication Data

US 2021/0121149 A1 Apr. 29, 2021

(30) Foreign Application Priority Data

Oct. 23, 2019 (DE) ..................... 10 2019 216 329.7

(51) Int. Cl.
*A61B 6/00* (2006.01)
*G06T 7/11* (2017.01)
(Continued)

(52) U.S. Cl.
CPC .............. *A61B 6/5282* (2013.01); *G06T 7/00* (2013.01); *G06T 7/0012* (2013.01); *G06T 7/11* (2017.01); *A61B 6/0407* (2013.01); *A61B 6/4441* (2013.01); *G06T 2207/10081* (2013.01); *G06T 2207/20076* (2013.01); *G06T 2207/20081* (2013.01); *G06T 2207/20084* (2013.01); *G06T 2207/30004* (2013.01)

(58) Field of Classification Search
CPC ... A61B 6/0407; A61B 6/4441; A61B 6/5282; G06N 3/0454; G06N 3/084; G06T 7/00; G06T 7/0012; G06T 7/11; G06T 11/006; G06T 11/008; G06T 2207/10081; G06T 2207/20076; G06T 2207/20081; G06T 2207/20084; G06T 2207/30004
See application file for complete search history.

(56) References Cited

U.S. PATENT DOCUMENTS

2008/0013673 A1 1/2008 Ruhmschopf
2018/0078221 A1 3/2018 Petersilka
(Continued)

FOREIGN PATENT DOCUMENTS

DE 102004029010 A1 1/2006
DE 102016217984 A1 4/2018
(Continued)

OTHER PUBLICATIONS

German Office Action for German Application No. 10 2019 216 329.7 dated Jul. 27, 2020.
(Continued)

*Primary Examiner* — Mark R Gaworecki
(74) *Attorney, Agent, or Firm* — Lempia Summerfield Katz LLC

(57) ABSTRACT

Systems and methods for quantification of an influence of scattered radiation in the analysis of an object a projection image is provided. Based on the projection image and on a characteristic of a tomography facility and/or of the object relating to the influence of the scattered radiation, at least one intermediate image is created. The at least one intermediate image is analyzed using an artificial neural network to quantify the influence of the scattered radiation.

19 Claims, 2 Drawing Sheets

(51) Int. Cl.
    *G06T 7/00*     (2017.01)
    *A61B 6/04*     (2006.01)

(56) References Cited

U.S. PATENT DOCUMENTS

| | | |
|---|---|---|
| 2018/0330233 A1 | 11/2018 | Rui et al. |
| 2019/0066268 A1 | 2/2019 | Song |
| 2020/0279410 A1 | 9/2020 | Lee |

FOREIGN PATENT DOCUMENTS

| | | |
|---|---|---|
| EP | 3637369 A1 | 4/2020 |
| WO | 2019103354 A1 | 5/2019 |

OTHER PUBLICATIONS

Maier, Joscha, et al. "Deep scatter estimation (DSE): accurate real-time scatter estimation for x-ray CT using a deep convolutional neural network." Journal of Nondestructive Evaluation 37.3 (2018): 57. pp. 1-9.

Maier, Joscha, et al. "Real-time scatter estimation for medical CT using the deep scatter estimation: Method and robustness analysis with respect to different anatomies, dose levels, tube voltages, and data truncation." Medical physics 46.1 (2019): 238-249.

Xu, Shiyu, et al. "Deep residual learning in CT physics: scatter correction for spectral CT." 2017 IEEE Nuclear Science Symposium and Medical Imaging Conference (NSS/MIC). IEEE, 2017. pp. 1-3.

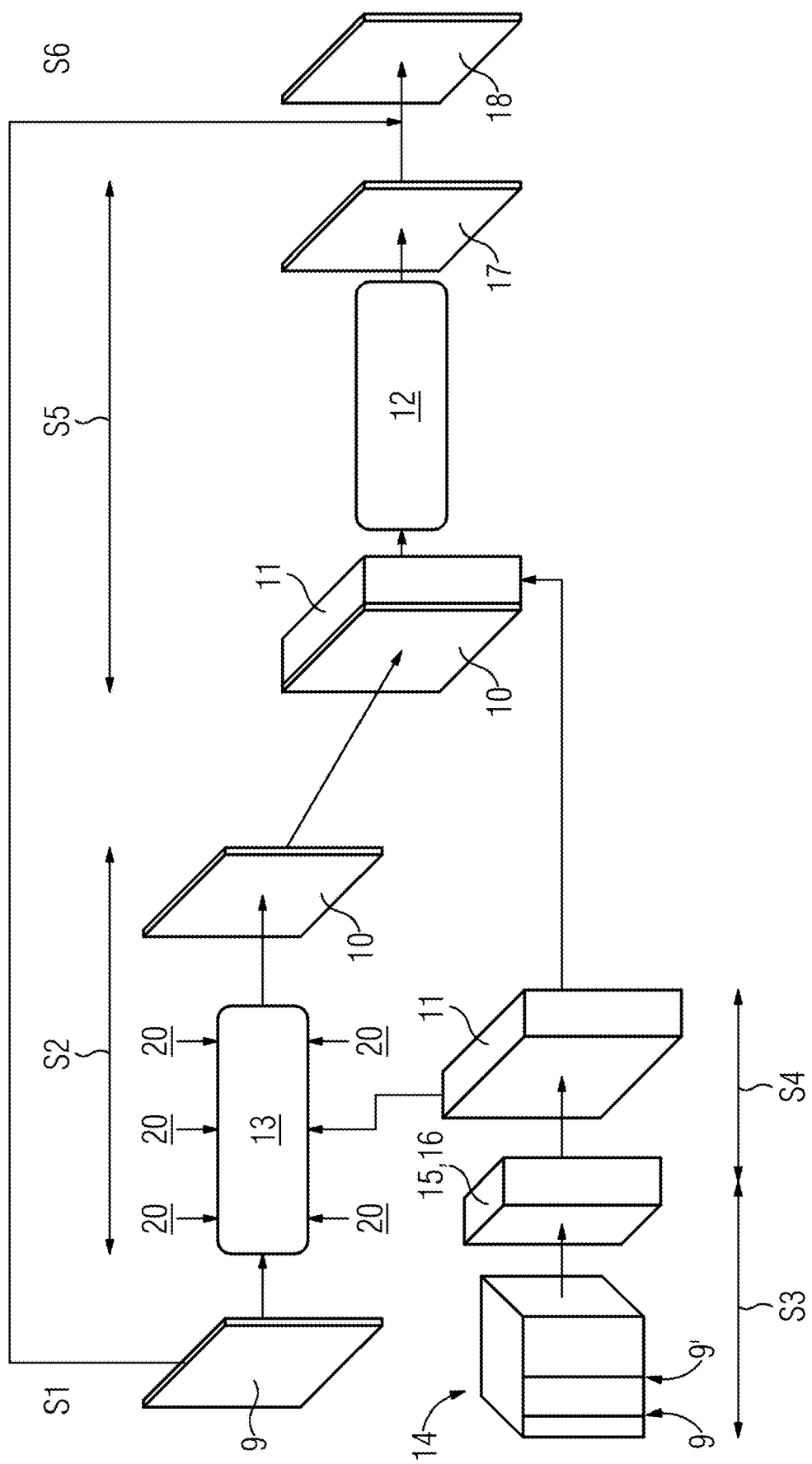

QUANTIFICATION OF AN INFLUENCE OF SCATTERED RADIATION IN A TOMOGRAPHIC ANALYSIS

CROSS REFERENCE TO RELATED APPLICATIONS

This patent document also claims the benefit of DE 102019216329.7 filed on Oct. 23, 2019 which is hereby incorporated in its entirety by reference FIELD Embodiments relate to a computer-implemented method for quantification of an influence of scattered radiation in a tomographic analysis of an object where a projection image of the object created by a tomography facility is provided.

BACKGROUND

In the tomographic analysis of objects in a medical or non-medical context, for example when using x-rays, i.e. in computed tomography or cone beam computed tomography methods for example, scattered radiation may lead to artifacts in the resulting images and accordingly to a reduced image quality.

To improve the image quality or to reduce the scattered radiation artifacts, the distribution of the scattered radiation may in principle be simulated by a simulation. Realistic physical simulations are not able to be employed in the productive context however, since as well as very high computational outlay, these require precise information about the material and density distribution of the analyzed object.

In model-based approaches a scattered radiation source image may be computed from the recorded projection images and for each pixel specifies scattered radiation caused by the measured x-ray radiation. The distribution of the scattered radiation may then be computed by convolution of the scattered radiation source image with a scattered radiation kernel. This is based on empirical models, that restricts the reliability and potential accuracy that may be achieved.

In the document entitled "Real-time scatter estimation for medical CT using the deep scatter estimation: Method and robustness analysis with respect to different anatomies, dose levels, tube voltages, and data truncation", Maier et al., Med. Phys. 46(1), January 2019, a method is presented in which, based on a projection image using a neural network, a scattered radiation estimate is computed. The accuracy of this method is also potentially restricted, since no system-specific information that would be required for a precise estimation is available to the neural network.

SUMMARY

The scope of the present invention is defined solely by the appended claims and is not affected to any degree by the statements within this summary. The present embodiments may obviate one or more of the drawbacks or limitations in the related art.

Embodiments provide for quantification of an influence of scattered radiation in a tomographic analysis of an object, by which the precision of the quantification may be increased.

Embodiments do not analyze the projection image that was created by a tomography facility directly with the neural network but create at least one intermediate image based on the projection image as a function of specific characteristics that relate to the tomography facility or the object, and analyze the image using the neural network.

Embodiments provide a computer-implemented method for quantification of an influence of scattered radiation in a tomographic analysis of an object. A projection image of the object created by a tomography facility is provided, for example to a computer unit. Based on the projection image and based on a characteristic of the tomography facility and/or of the object relating to the influence of the scattered radiation, on the projection image for example, at least one intermediate image is created by the computer unit. The at least one intermediate image is analyzed by the computer unit using, for example, a trained artificial neural network, to quantify the influence of the scattered radiation.

The influence of the scattered radiation may be understood for example as the influence of the scattered radiation on the tomographic analysis or on a result of the tomographic analysis, for example on the projection image, on further projection images or on slice images of the object created based on the projection images.

The tomographic analysis may correspond for example to analysis by a computed tomography method, CT, or a digital volume tomography method, DVT, or a cone beam computed tomography method, CBCT.

Accordingly, the projection image contains a matrix including measured values for example, also referred to as pixel values, that are created by a detector of the tomography facility based on the radiation passing through the object and thereby attenuated accordingly, for example x-ray radiation.

The pixel values may also be referred to or understood as line integrals, since for example the pixel values correspond to integrated attenuation values on a path through the object. The path depends on the concrete beam direction of the radiation.

The provision of the projection image may be understood for example in such a way that the projection image or the matrix of pixel values is provided to the computer unit on a storage medium, for example a storage medium of the computer unit.

The creation of the projection image by the tomography facility may be part of the method for quantification of the influence of the scattered radiation or may be undertaken before the method.

The characteristic of the tomography facility and/or of the object includes one or more measurable parameters of other variables able to be specified in numerical values relating to the object, the execution of the tomographic analysis and/or the tomography facility. The characteristic may relate for example to parameters or other values relating to a composition, structure, density distribution or material distribution of the object. The characteristic may for example include scalar variables, vectors and/or one or more matrixes, for example images. The characteristic may contain one or more operating parameters of the tomography facility for carrying out the tomographic analysis, that are able to be set for example, such as for example operating voltages and the like, as well as parameters predetermined by construction or by being fixed in some other way.

The particular common factor in all parameters, values or contents of the characteristic in this case is that their actual value relates to the influence of the scattered radiation on the result of the tomographic analysis, i.e. depending on the value of the corresponding parameter or of numerical values, the result is various discrepancies between the projection image and a theoretical ideal projection image entirely free of scatter radiation effects.

The quantification of the influence of the scattered radiation may be understood as the creation or specifications of a description of the influence of the scattered radiation in computer-readable and machine-processable form.

For example, the result of the quantification may include one or more numerical values, for example a matrix consisting of numerical values, for example a scattered radiation image. The scattered radiation image depends in this case on the influence of the scattered radiation.

To completely or partly compensate for the influence of the scattered radiation the projection image may be modified for example as a function of the scattered radiation image or the other results of the quantification, to create a compensated projection image, that is freed at least partly from the influence of the scattered radiation.

A neural network may be understood as a computer or software algorithm or as a part of a software algorithm, that creates an output based on input data.

The output of the neural network based on the analysis of the intermediate image may be seen as a result of the analysis by the neural network and may be understood as a measure of the influence of the scattered radiation on the projection image. The analysis of the at least one intermediate image using the neural network thus corresponds for example to the quantification of the influence of the scattered radiation. For example, the output of the neural network may correspond to the scattered radiation image or the scattered radiation image may be derived directly from the output of the neural network.

The artificial neural network is trained for example using a training method before being used for analysis of the at least one intermediate image. To this end the neural network may receive training data as input data for example and the output of the neural network based on the training data may be compared with predetermined reference data to train the neural network.

The reference data in this case is determined on the basis of a model, a simulation and/or an empirical method for example and describes an influence of the scattered radiation on the training data.

High-quality reference data may be created for training the network by for example analyzing a training object of which the internal structure is known, to create the training data.

Explicitly taking account of the characteristics of the tomography facility and/or of the object provides a higher precision in the quantification of the influence of the scattered radiation to be achieved than would be possible with direct analysis of the projection image by a neural network.

A complete physical simulation of the tomographic analysis is not required for the productive phase of the method. For example, such an analysis may be employed for a training phase for training the artificial neural network. Training objects may be employed to advantage here of which the structure, for example their material and density distributions, are known.

The productive phase on the other hand may be conducted in a very much shorter time and with very much less computational outlay than the complete simulation.

By comparison with empirical models for estimation of the influence of the scattered radiation, the embodiments likewise deliver a higher accuracy without a calibration of the method having been required.

In an embodiment the artificial neural network is configured as a convolutional neural network, CNN.

Such architectures of neural networks are especially well suited to the analysis of two-dimensional datasets, such as represent digital images.

In an embodiment the method for quantification of the influence of the scattered radiation includes the creation of the projection image by the tomography facility.

In an embodiment the tomographic analysis is configured as x-ray based tomographic analysis, for example as CT analysis, for example as CBCT analysis. Accordingly, the tomography facility is configured as an x-ray tomography facility, for example CT facility or CBCT facility.

In an embodiment the projection image is analyzed, for example by the computer unit, using a further artificial neural network depending on at least one parameter of the tomography facility, to create a scatter source image, and the at least one intermediate image contains the scatter source image.

The characteristic of the tomography facility, for example, includes the at least one parameter of the tomography facility.

The scatter source image is, for example, an output of the further neural network or is able to be derived directly from the output of the further neural network.

The at least one parameter and at least one-pixel value of the projection image are used as input variables of the further neural network.

Because of the explicit, upstream, and separate taking account of the parameters of the tomography facility a higher accuracy and efficiency may be achieved. Moreover, account may be taken of a greater variance or bandwidth of the values of the at least one parameter that might be used.

In an embodiment the at least one parameter of the tomography facility contains a voltage, for example an x-ray voltage for creating the x-ray radiation, an irradiation during the creation of the projection image, a cone angle during the creation of the projection image in the case of CBCT or a fan angle of the x-ray beam in the case of conventional CT, a measure for a collimation of the x-ray beam and/or a value of an air gap, for example between the object and the detector.

In accordance with at least one form of embodiment the further artificial neural network is configured as a fully connected neural network. A fully connected neural network may be a neural network that does not have any convolutional layers but for example exclusively fully connected layers.

In an embodiment the projection image is analyzed using the further neural network pixel-by-pixel depending on the at least one parameter.

In an embodiment a material-specific projection image is created by the computer unit based on the projection image or based on a further projection image of the object created by the tomography facility. The at least one intermediate image contains the material-specific projection image.

The material-specific projection image corresponds in this case to a projection image of the object in which only one specific material or a specific group of materials of the object is taken into account.

The characteristic of the object contains for example the at least one material-specific projection image.

The material-specific projection image for example explicitly takes into account material and/or density distributions of the object, that is not possible in general for example in simulation-based approaches. Through this a higher accuracy of the end result of the quantification is achieved.

In embodiments in which the material-specific projection image and the scatter source image are created, the at least one intermediate image accordingly contains both the material-specific projection image and also the scatter source image.

In an embodiment a signal reconstruction is carried out by the computer unit based on the projection image or based on the further projection image to create a slice image. The material-specific projection image is created based on the slice image by the computer unit.

The signal reconstruction takes place for example based on a plurality of projection images, that includes the projection image and/or the further projection image, for example based on all available projection images created by the tomography facility for tomographic analysis of the object. The individual projection images of the plurality of projection images correspond for example in this case to different beam angles during the recording.

The signal reconstruction may be understood as backprojection and for example includes the computation of the corresponding attenuation values from the line integrals or pixel values of the plurality of pixel images.

In an embodiment the slice image is segmented by the computer unit, to create a material-specific slice image and the material-specific projection image is created by the computer unit based on the material-specific slice image.

Each slice image in this case may deliver an associated material-specific slice image for one or more predetermined materials or groups of material in each case.

The segmentation, i.e. the division of the slice image into the different material-specific slice images, may be performed using a threshold analysis or using a classifier, for example based on a neural network.

The material-specific projection image is created based on the material-specific slice image in this case for example by forwards projection of the material-specific slice image and possibly further material-specific slice images.

For example, based on the plurality of projection images, a plurality of slice images may be created by backprojection and all slice images created in this way may be segmented to obtain corresponding sets of material-specific slice images. Each set corresponds to one material or to one group of materials.

The forward projection is a forward projection of a set of material-specific slice images, for example, the calculation of line integrals from the corresponding material-specific attenuation values. Various fictional x-ray beam directions are assumed.

In an embodiment an approximated scatter image is created by the computer unit based on the projection image or the further projection image and the material-specific projection image, for example the slice image, depending on the approximated control image.

The approximated scatter image corresponds for example to a scatter image that approximately describes the influence of the scattered radiation, for example based on an empirical model.

For example, the approximated scatter image is created based on the projection image and a partly compensated projection image is created by setting the approximated scatter image off against the projection image. Then, based on the partly compensated projection image, the slice image is created by backward projection, as described above.

The fact that the scatter effects are already approximately taken into account for creating the material-specific projection image and correspondingly the at least one intermediate image enables a higher accuracy and an improved efficiency of the quantification to be achieved.

In an embodiment the projection image is analyzed, for example by the computer unit, using the further neural network depending on the material-specific projection image, to create the scatter source image.

The analysis is undertaken for example in this case, as described above, pixel-by-pixel. The at least one parameter of the tomography facility, a pixel of the projection image and also a corresponding pixel of the material-specific projection image or if necessary, of further material-specific projection images serve as input variables for the further neural network.

Through this the tomography facility-specific and the object-specific characteristics for creating the intermediate image are coupled to obtain a further increase in efficiency and higher accuracy.

In an embodiment a compensated projection image is created by the computer unit based on the projection image and based on a result of the analysis of the intermediate image using the neural network, for example in respect of the scattered radiation.

The result of the analysis of the intermediate image may correspond for example to a scatter image or a scattered radiation image. The pixel values of the projection image may be multiplied by the corresponding pixel values of the scatter image for example, be divided by the corresponding pixel values of the scatter image, or the pixel values of the scatter image may be subtracted from the pixel values of the projection image, to create the compensated projection image. Other options may also be employed for setting the scatter image off against the projection image.

By comparison with the projection image, the compensated projection image is, for example, less heavily influenced by the scattered radiation, in the ideal case the influence of the scattered radiation is removed completely.

The compensated projection image accordingly includes fewer artifacts caused by scattered radiation than the projection image. Accordingly, a better image quality of slice images based on the projection image created by backprojection is obtained. For example, artifacts such as streak artifacts may be reduced in the slice images.

In an embodiment a compensated slice image is created by the computer unit based on the compensated projection image, for example by signal reconstruction, i.e. backprojection.

Embodiments provide a method for tomographic analysis of an object that contains a method for quantification of an influence of scattered radiation where the projection image is created and provided by the tomography facility.

For creation of the projection image, radiation is generated, for example by a radiation source, for example an x-ray source, and directed through the object. Attenuated portions of the radiation passing through the object are detected by a detector of the tomography facility and pixel values that represent the projection image are created on the basis thereof.

In an embodiment, a computer-implemented method for training a software algorithm, that includes at least one artificial neural network, is provided. A training projection image of a training object created by a tomography facility is provided or the training projection image is created by the tomography facility. At least one intermediate training image is created by a computer unit, based on the training projection image and a characteristic of the tomography facility and/or of the training object relating to an influence of scattered radiation. The at least one intermediate training image is analyzed on the basis of the software algorithm by the computer unit, to quantify the influence of the scattered radiation. A result of a simulation is provided. The simulation relates to the influence of the scattered radiation. A result of the analysis is compared by the computer unit with the result of the simulation and the at least one neural network is modified depending on a result of the comparison, to train the software algorithm.

The neural network may be a computer algorithm or software algorithm or as a part of the software algorithm.

The modification of the at least one neural network may include the changing of weighting factors of the at least one neural network.

Carrying out the simulation may be part of the method or may be done prior to using the method.

In an embodiment the method for training the software algorithm includes carrying out the simulation. The simulation simulates the creation of the training projection image by the tomography facility.

In an embodiment the simulation contains a Monte Carlo simulation of the creation of the training projection image by the tomography facility.

The simulation may, for example, be carried out by the computer unit or by a further computer unit.

Using the Monte Carlo simulation, the entire tomographic analysis may be physically simulated. Through this scatter effects may also be taken into account, so that the influence of the scattered radiation on the creation of the training projection image may be extracted with high accuracy.

The carrying out of the Monte Carlo simulation is possible because it relates to a training object. For example, material and/or density information of the training object is known, for example material or density distributions. This information may be taken into account in the Monte Carlo simulation.

Carrying out the Monte Carlo simulation may be processing-intensive depending on the complexity of the object and of the tomography facility. This is acceptable however, since the simulation is merely required during the training phase of the artificial neural network and no longer during the productive phase, for example carrying out a method for quantification of the influence of the scattered radiation or for tomographic analysis of an object.

The at least one neural network may for example include the neural network for analysis of the intermediate image in accordance with a method for quantification of the influence of the scattered radiation and, the further neural network for analysis of the projection image depending on the at least one parameter of the tomography facility.

In an embodiment of the method for quantification of the influence of scattered radiation, the neural network is or has been trained in accordance with a method for training a software algorithm according to an embodiment.

In an embodiment of the method for quantification of the influence of scattered radiation, the further neural network is or has been trained in accordance with a method for training a software algorithm according to an embodiment.

Further forms of embodiment of the method for training a software algorithm follow directly from the various forms of embodiment of the method for quantification of the influence of the scattered radiation and the associated embodiments and vice versa.

In an embodiment, a system for tomographic analysis of an object is provided. The system includes a tomography facility, that is configured to create a projection image of the object. The system includes a computer unit, that may be a component of the tomography facility for example and is configured, based on the projection image and a characteristic of the tomography facility and/or of the object relating to the influence of the scattered radiation, to create at least one intermediate image. The computer unit is configured to analyze the at least one intermediate image using an artificial neural network, to quantify the influence of the scattered radiation.

In an embodiment, the system, for example the computer unit, contains a storage medium on which a software algorithm is stored, that contains the neural network. The software algorithm is trained according to an embodiment described herein.

Further embodiments of the system follow from the various forms of embodiment of the various methods and vice versa in each case. For example, the system is configured or programmed to carry out a method for quantification of an influence of scattered radiation and/or a method for training a software algorithm or the system carries out such a method.

In an embodiment, a first computer program with first instructions is specified. When the first instructions are executed by a computer system, for example by a system, for example the computer unit of the system, the first instructions cause the computer system to carry out a method for quantification of the influence of the scattered radiation and/or a method for training a software algorithm.

In an embodiment, a second computer program with second instructions is specified. The second instructions, when the second computer program is executed by a system, cause the system to carry out a method for tomographic analysis of an object.

In an embodiment, a computer-readable storage medium is specified, on which a first computer program and/or a second computer program are stored.

The first and the second computer program as well as the computer-readable storage medium may each be referred to as the computer program product.

The features and combinations of features specified above in the description as well the features and combinations of features given below in the description of the figures and/or solely in the figures are able to be used not only in the combination specified in each case but also in other combinations, without departing from the framework. Combinations of features are also to be seen as disclosed that do not have all features of an originally formulated independent claim and/or that go beyond the combinations of features set out in the references of the claims or deviate from the references.

BRIEF DESCRIPTION OF THE FIGURES

FIG. 2 depicts a flow diagram of an embodiment of a method for quantification of the influence of scattered radiation.

DETAILED DESCRIPTION

Figure 1:
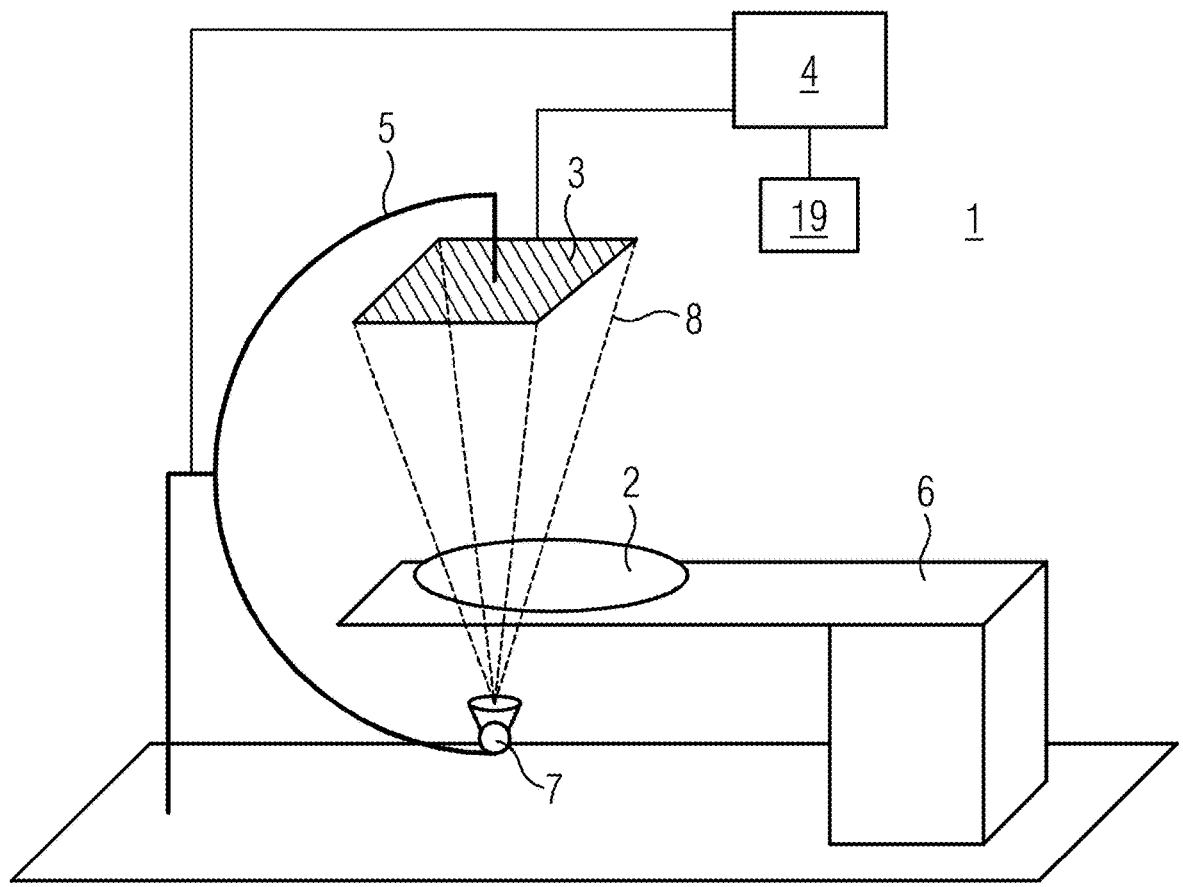
FIG. 1 depicts a schematic diagram of an embodiment of a system for tomographic analysis of an object.

FIG. 1 depicts a schematic diagram of an embodiment of a system for tomographic analysis of an object 2.

The system includes a tomography facility 1, that may be configured as a CBCT facility for example. The tomography facility 1 is configured for example as a C-arm CT facility.

The tomography facility 1 includes a detector 3, that for example may contain a two-dimensional array of picture elements or pixels. The detector 3 may be arranged at one end of a C-arm 5 of the tomography facility 1 for example.

The tomography facility 1 also includes a radiation source 7, for example an x-ray source, that may be arranged at an opposite end of the C-arm 5 to the detector 3 for example.

The tomography facility 1 includes a computer unit 4, that is coupled to the detector 3 and may be coupled to the C-arm 5 to control its movement. The computer unit 4 may also be coupled to the radiation source 7 to control the latter. As an alternative other control devices or computing units may take over the tasks of controlling the C-arm 5 and/or the radiation source 7.

The computer unit 4 includes a storage element 19, on which an artificial neural network, for example a CNN 12 (see FIG. 2) and, for example, a further artificial neural network, for example a fully connected network 13 (see FIG. 2), are stored.

A support 6 is depicted in FIG. 1 on which the object 2 may be arranged. The C-arm 5 may for example be controlled in such a way that the object 2 is located between the radiation source 7 and the detector 3. In operation of the tomography facility 1 the radiation source 7 may generate x-ray radiation 8, for example a cone-shaped bundle of x-rays, that at least partly pass through the object 2 and strike the detector 3 in a correspondingly attenuated form.

Depending on the spatially varying radiation power, that falls on the individual pixels of the detector 3, the detector 3 creates corresponding measured values and transmits the values to the computer unit 4.

The function of the tomography facility 1 is explained below using an example of a method for quantification of the influence of scattered radiation.

FIG. 2 depicts a flow diagram of an embodiment of a method for quantification of an influence of scattered radiation.

In step S1 of the method a projection image 9 of the object 2 created by the tomography facility 1 is provided. The measurement data as explained in relation to FIG. 1 is created and transmitted to the computer unit 4. The computer unit 4, based on the measurement data, may then create a plurality of projection images 14, that the projection image 9 contains.

The subsequent steps S2 to S4 are not necessarily all required to carry out the method. For example, the method may not feature the steps S3 and S4 or the method may not feature the step S2. However, the method features either the step S2 or the steps S3 and S4 or all steps S2 to S4.

The subsequent steps S2 to S4 describe the creation of at least one intermediate image 10, 11 by the computer unit 4 based on the projection image 9 and a characteristic of the tomography facility 1 and/or of the object 2, that relates to the influence of the scattered radiation on the creation of the projection image 9. The steps S2 to S4 are discussed in greater detail below.

The at least one intermediate image 10, 11 is analyzed in step S5 of the method using the CNN 12. For example, the at least one intermediate image 10, 11 is used as input for the CNN 12, that creates a scattered radiation image 17 based thereon. The scattered radiation image 17 in this case reflects respective portions of the pixel values of the projection image 9 that are caused by the scattered radiation.

The CNN 12 is trained accordingly in an upstream training method, for example according to an embodiment described herein. For example, a Monte Carlo simulation of a tomographic CBCT analysis of a training object, of which the density and material distribution is known, is carried out. Based on the Monte Carlo simulation a simulated scattered radiation image is created and compared with an output of the CNN 12, to adapt the weights of the CNN 12 by back propagation and to train the CNN 12 accordingly.

In step S6 the computer unit 4 sets the scattered radiation image 17 off against the projection image 9, to obtain a compensated projection image 18. The computer unit 4 may, for example, take the pixel values of the scattered radiation image 17 away from the pixel values of the projection image 9, to obtain the compensated projection image 18. As an alternative or in addition the computer unit carries out multiplication or division operations.

In step S2 the projection image 9 is analyzed pixel-by-pixel using the fully connected network 13, to create a scatter source image 10. The analysis is undertaken in this case, as well as dependent on a pixel of the projection image 9, dependent on a function of at least one parameter 20 of the tomography facility 1. The at least one parameter 20 may, for example, include an x-ray voltage, an air gap, a cone angle, a beam angle corresponding to the projection image 9, a level of collimation and so forth for the creation of the measurement data, for example of the projection image 9. The analysis is carried out for example for each pixel of the projection image 9.

The fully connected network 13 may also be trained during the upstream training phase using a similar process to that described above in relation to the CNN 12. For example, the CNN 12 and the fully connected network 13 may be trained jointly.

The scatter source image 10 is a component of the at least one intermediate image 10, 11.

In step S3 and S4 a plurality of material-specific projection images 11 are created by the computer unit 4 based on the plurality of projection images 14, i.e. for example based on the projection image 9 and a further projection image 9'. The material-specific projection images 11 are likewise a component of the at least one intermediate image 10, 11.

The computer unit 4 may carry out a signal reconstruction in step S4 based on the plurality of projection images 14, to create a corresponding plurality of slice images 15 of a volume of the object 2.

The computer unit 4 moreover segments in step S3 the at least one slice image corresponding to various materials of the object 2, to obtain a plurality of material-specific slice images 16.

In this case the computer unit 4 may undertake a threshold value analysis of the attenuation values of the plurality of slice images 15 for example, to divide them into different materials or groups of material.

The plurality of material-specific slice images 16 is then projected forwards in step S4 by the computer unit, to obtain the plurality of material-specific projection images 11.

Embodiments provide a more precise quantification of the influence of scattered radiation on the tomographic analysis of an object to be achieved.

With cone beam computed tomography, for example, it is advantageous to take account of the scattered radiation artifacts in the analysis of the object. This provides the image quality to be decisively improved during tomographic analysis.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer implemented method for quantification of an influence of scattered radiation in a tomographic analysis of an object, the method comprising:
acquiring a projection image of the object created by a tomography facility;
creating, by a computer unit, at least one intermediate image based on both of the projection image and a pre-defined characteristic, wherein the pre-defined characteristic is a characteristic of the tomography facility, of the object relating to the influence of the scattered radiation, or of the tomography facility and of the object relating to the influence of the scattered radiation; and
analyzing the at least one intermediate image by an artificial neural network to quantify the influence of the scattered radiation.

2. The computer implemented method of claim 1, further comprising:
analyzing the projection image using a further artificial neural network depending on at least one parameter of the tomography facility to create a scatter source image, wherein the at least one intermediate image includes the scatter source image.

3. The computer implemented method of claim 1, further comprising:
creating, by the computer unit, a material-specific projection image based on the projection image or a further projection image of the object created by the tomography facility;
wherein the at least one intermediate image contains the material-specific projection image.

4. The computer implemented method of claim 3, further comprising:
carrying out, by the computer unit, a signal reconstruction based on the projection image or the further projection image to create a slice image;
wherein the material-specific projection image is created based on the slice image.

5. The computer implemented method of claim 4, further comprising:
segmenting, by the computer unit, the slice image to create a material-specific slice image;
wherein the material-specific projection image is created based on the material-specific slice image.

6. The computer implemented method of claim 4, further comprising:
creating an approximated scatter image based on the projection image or the further projection image;
wherein the material-specific projection image is created based further on the approximated scatter image.

7. The computer implemented method of claim 4, further comprising:
analyzing the projection image using a further artificial neural network depending on at least one parameter of the tomography facility to create a scatter source image, wherein the at least one intermediate image includes the scatter source image;
wherein the projection image is analyzed using the further artificial neural network depending on the material-specific projection image to create the scatter source image.

8. The computer implemented method of claim 1, further comprising:
generating a compensated projection image by the computer unit based on the projection image and on a result of the analysis of the intermediate image.

9. A computer-implemented method for training of an at least one artificial neural network, the method comprising:
acquiring a training projection image of a training object;
creating at least one intermediate training image based on both of the training projection image and a pre-defined characteristic, wherein the pre-defined characteristic is a characteristic of a tomography facility, of the training object relating to an influence of scattered radiation, or of the tomography facility and of the training object relating to the influence of scattered radiation; and
analyzing the at least one intermediate training image to quantify the influence of the scattered radiation;
providing a result of a simulation that relates to the influence of the scattered radiation;
comparing a result of the analysis with the result of the simulation; and
modifying the at least one artificial neural network depending on a result of the comparison in order to train the at least one artificial neural network.

10. The computer-implemented method of claim 9, wherein the simulation includes a Monte Carlo simulation for creating the training projection image.

11. The computer-implemented method of claim 9, further comprising:
acquiring a projection image of an object created by a tomography facility;
creating at least one intermediate image based on the projection image and the pre-defined characteristic; and
analyzing the at least one intermediate image by the at least one artificial neural network to quantify the influence of the scattered radiation.

12. A system for tomographic analysis of an object, the system comprising:
a tomography facility configured to create a projection image of the object; and
a computer unit configured to create at least one intermediate image based on the projection image and a predefined characteristic, wherein the predefined characteristic is a characteristic of the tomography facility, of the object relating to an influence of scattered radiation, or of the tomography facility and of the object relating to the influence of the scattered radiation, the computer unit further configured to analyze the at least one intermediate image using an artificial neural network to quantify the influence of the scattered radiation.

13. The system of claim 12, further comprising:
a non-transitory storage medium configured to store a software algorithm that includes the artificial neural network.

14. The system of claim 13, wherein the artificial neural network is trained using an iterative method comprising:
acquiring, by the tomography facility, a training projection image of a training object;

creating, by the computer unit, at least one intermediate training image based on the training projection image and the predefined characteristic;

analyzing, by the computer unit using the artificial neural network, the at least one intermediate training image to quantify the influence of the scattered radiation;

providing, by the computer unit, a result of a simulation that relates to the influence of the scattered radiation;

comparing, by the computer unit, a result of the analysis with the result of the simulation; and modifying, by the computer unit, the artificial neural network depending on a result of the comparison in order to train the software algorithm.

15. The system of claim 12, wherein the computer unit is further configured to analyze the projection image using a further artificial neural network depending on at least one parameter of the tomography facility to create a scatter source image, wherein the at least one intermediate image includes the scatter source image.

16. The system of claim 12, wherein the computer unit is further configured to create a material-specific projection image based on the projection image or a further projection image of the object created by the tomography facility; wherein the at least one intermediate image contains the material-specific projection image.

17. The system of claim 16, wherein the computer unit is further configured to carry out a signal reconstruction based on the projection image or the further projection image to create a slice image; wherein the material-specific projection image is created based on the slice image.

18. The system of claim 17, wherein the computer unit is further configured to segment the slice image to create a material-specific slice image; wherein the material-specific projection image is created based on the material-specific slice image.

19. The system of claim 17, wherein the computer unit is further configured to create an approximated scatter image based on the projection image or the further projection image; wherein the material-specific projection image is created based further on the approximated scatter image.

* * * * *